US008618077B2

(12) United States Patent
Jin et al.

(10) Patent No.: US 8,618,077 B2
(45) Date of Patent: Dec. 31, 2013

(54) COMPOSITIONS AND METHODS FOR TREATING FRAGILE X PREMUTATION RVGG REPEATS-MEDIATED TOXICITY

(75) Inventors: Peng Jin, Decatur, GA (US); Abrar Qurashi, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 13/457,718

(22) Filed: Apr. 27, 2012

(65) Prior Publication Data
US 2012/0277178 A1 Nov. 1, 2012

Related U.S. Application Data

(60) Provisional application No. 61/479,968, filed on Apr. 28, 2011.

(51) Int. Cl.
*A61K 31/7068* (2006.01)
(52) U.S. Cl.
USPC .................................................. 514/51
(58) Field of Classification Search
USPC .................................................. 514/51
See application file for complete search history.

(56) References Cited

PUBLICATIONS

Qurashi et al. Identification of small molecules suppressing rCGG-repeat-mediated neurodegeneration. American Society of Human Genetics Annual Meeting, Abstract, 2008.*
Torrioli et al. Double-Blind, Placebo-Controlled Study of L-Acetylcarnitine for the Treatment of Hyperactive Behavior in Fragile X Syndrome. Am J Med Genet 87:366-368, 1999.*
Balsinde, J, et al., 1999, Regulation and Inhibition of Phospholipase A2, Annu. Rev. Phamacol. Toxicol., 39: 175-89.
Calabrese, V., et al., 1998, Redox Homeostasis and Cellular Stress Response in Aging and Neurodegeneration, Free Radicals and Antioxidant Protocols, Methods in Molecular Biology 610, Humana Press, Chapter 17; 285-308.
Conant, R, et al., 2004, Therapeutic Applications of Citicoline for Stroke and Cognitive Dysfunction in the Elderly: A Review of the Literature, Alternative Medicine Review, 9 (1): 17-31.
Farooqui, A., et al., 2006, Inhibitors of Brain Phospholipase A2 Activity: Their Neuropharmacological Effects and Therapeutic Importance for the Treatment of Neurologic Disorders, Pharmacological Reviews, 58 (3):591-620.

Ferro, M., et al., 2007, Neuroprotective effect of ketamine/xylazine on two rat models of Parkinson's disease, Brazilian Journal of Medical and Biological Research, 40:89-96.
Glybina, I, et al., Intravitreous Delivery of the Corticosteroid Fluocinolone Acetonide Attenuates Retinal Degeneration in S334ter-4 Rats, Investigative Ophthalmology & Visual Science, 51 (8): 4243-4252.
Hagerman, R., et al., 2008, Review; Treatment of Fragile X-associated Tremor Ataxia Syndrome (FXTAS) and related neurological problems, Clincal Interventions in Aging, 3 (2): 251-261.
Hirth, Frank, 2010, *Drosophila melanogaster* in the Study of Human Neurodegeneration, CNS & Neurological Disorders-Drug Targets, 9: 504-523.
Huo, Y., et al., 2011, Research Article: Dexamethasone inhibits the Nox-dependent ROS production via suppression of MKP-1-dependent MAPK pathways in activated microglia, BMC Neuroscience, 12: 49.
Kim, M., et al, Aug. 2011, Protective effects of a chalcone derivative against Aβ-induced oxidative stress and neuronal damage, BMB Reports; 730-734.
Lessing, D., et al., 2009, Review: Maintaining the brain: insight into human neurodegeneration from *Drosophila melanogaster* mutants, Genetics, 10:359-370.
Pfeiffenberger, C, et al., 2010, Locomotor Activity Level Monitoring Using the *Drosophila* Activity Monitoring (DAM) System, Adapted from *Drosophila* Neurobiology (ed. Zhang et al.). CSHL Press, Cold Spring Harbor, NY, USA, 2010, pp. 1238-1241.
Qurashi, A., et al., 2011, Nuclear Accumulation of Stress Response mRNAs Contributes to the Neurodegeneration Caused by Fragile X Premutation rCGG Repeats, PLOS Genetics, 7 (6) e1002102.
Qurashi, A., et al., 2012, Chemical screen reveals small molecules suppressing fragile X premutation rCGG repeat-mediated neurodegeneration in *Drosophila*, HMG Advance Access. Published by Oxford University Press.
Seungdamrong, A., et al., 2008, Fragile X for the Obstetrician and Gynecologist, Expert Reviews. Obstet. Gynecol 3 (6): 761-766.
Tariq, M, et al., 2001, Protective effect of quinacrine on striatal dopamine levels in 6-OHDA and MPTP models of Parkinsonism in rodents, Brain Research Bulletin, 54 (1):77-82.
Todd, P., et al., 2010, Neurological Progress; RNA-Mediated Neurodegeneration in Repeat Expansion Disorders, Annals of Neurology, 67 (3): 291-300.
Zhang, H., et al., 2010, Combined R-alpha-lipoic acid and acetyl-L-car exerts efficient preventative effects in a cellula model of Parkinson's disease, Abstract, J Cell Mol Med, 14 (1-2) :215-225.

\* cited by examiner

*Primary Examiner* — Wu-Cheng Winston Shen
*Assistant Examiner* — Yih-Horng Shiao
(74) *Attorney, Agent, or Firm* — Emory Patent Group; James C. Mason; Susanne Hollinger

(57) ABSTRACT

Compositions and methods of treatment or prophylaxis of fragile-X associated disorders are provided, as well as methods of screening compounds and kits to screen a library of compounds.

3 Claims, 8 Drawing Sheets

Locomotion Assay

Crosses raised in the food with individual compound from the small molecule library nervana-Gal4/Cyo   ×   UAS-CGG$_{90}$-EGFP/Cyo nervana-Gal4/Cyo nervana-Gal4/ UAS-CGG$_{90}$-EGFP Locomotion deficits due to UAS-CGG$_{90}$-EGFP

COMPOSITIONS AND METHODS FOR TREATING FRAGILE X PREMUTATION RVGG REPEATS-MEDIATED TOXICITY

CROSS-REFERENCE TO RELATED APPLICATIONS

This application claims priority to U.S. Provisional Application No. 61/479,968 filed 28 Apr. 2011, hereby incorporated by reference in its entirety.

FIELD

The present disclosure is generally directed to compounds, compositions, and methods of treatment or prevention of Fragile X associated disorders, including Fragile X-associated tremor/ataxia syndrome (FXTAS).

BACKGROUND

The CGG repeat expansion in the 5'-UTR of the fragile X mental retardation gene (FMR1) has been implicated in the pathogenesis of two distinct disorders, fragile X syndrome (FXS), a neurodevelopmental disorder and fragile X-associated tremor and ataxia syndrome (FXTAS), a progressive neurodegenerative disease that is usually late onset. While normal individuals generally possess between 5 and 54 CGG repeats, fully affected individuals have more than 200 CGG repeats on what are referred to as "full mutation alleles." "Pre-mutation alleles" (55-200 CGG repeats) of the FMR1 gene are known to contribute to the fragile X phenotype through genetic instability and could expand into full mutation during germline transmission.

FXTAS has been recognized among many male pre-mutation carriers in or beyond their fifth decade of life and is uncoupled from the FXS neurodevelopmental disorder. Although both disorders involve repeat expansions in the FMR1 gene, the clinical presentation and molecular mechanisms underlying each disease are distinct. The most common clinical feature of FXTAS is a progressive action tremor with ataxia. More advanced or severe cases may show a progressive cognitive decline that ranges from executive and memory deficits to dementia. Patients may also present with common psychiatric symptoms such as increased anxiety, mood liability and depression. Patients also complain of fluctuating muscle weakness and numbness and/or pain in the lower extremities, which suggests the disease may not be purely neurological.

Magnetic resonance imaging (MRI) of adult male patients affected with FXTAS demonstrated mild to moderate global brain atrophy, most common in the fontal and parietal regions as well as the pons and cerebellum. The most significant radiological findings were the increased T2 intensities of the middle cerebellar peduncle (MCP) and adjacent cerebellar white matter not seen in controls.

Nearly all case studies on autopsy brains of symptomatic premutation carriers demonstrated degeneration in the cerebellum, including Purkinje neuronal cell loss, Bergman gliosis, spongiosis of the deep cerebellar white matter and swollen axons. The major neuropathological hallmark and postmortem criterion for definitive FXTAS is eosinophilic, ubiquitin-positive intranuclear inclusions located in broad distribution throughout the brain in neurons, astrocytes, and in the spinal column. The inclusions are both tau and α-synuclein negative, which indicates that FXTAS is not a tauopathy or synucleinopathy. The FXTAS inclusions share the ubiquitin positive hallmark with several other inclusion disorders, such as polyglutamine disorders, although the inclusions do not stain with antibodies that recognize polyglutamine, which suggests a defect in the proteasomal degradation pathway. Unlike the polyglutamine disorders, there is no known structurally abnormal protein produced in FXTAS (the premutation is non-coding).

An RNA gain-of-function mechanism has been suggested for FXTAS based on the observation of increased levels of CGG-containing FMR1 mRNA, along with either reduced FMRP in premutation carriers. The absence of FXS, which results from the loss of function of the FMR1 gene product, in FXTAS patients along with absence of symptoms in older individuals with FXS also suggests a role for the expanded ribo-CGG (rCGG) repeat in FXTAS pathology. This type of RNA gain of function mechanism has been suggested as a mechanism for triplet repeat-related ataxias such as SCA8, SCA10, and SCA12 and in myotonic dystrophy (DM). The untranslated repeat expansion in DM has offered major insight into the underlying molecular mechanisms of FXTAS. DM1 is caused by a CTG repeat expansion in a region of transcribed RNA, but not translated into protein, the 3'UTR of the DMPK gene. The mutant transcripts sequester certain proteins, which form ribonuclear foci or inclusions.

Several additional lines of evidence further support an RNA-mediated gain-of-function toxicity model for FXTAS. First, in a "knock-in" mouse model designed with a ~100 CGG repeat fragment, intranuclear inclusions were found to be present throughout the brain. An increase in both the number and size of the inclusions was observed during the life course, which correlates with the progressive character of the phenotype observed in humans. Neuropathological studies in humans have revealed a highly significant association between length of the CGG tract and frequency of intranuclear inclusions in both neurons and astrocytes, indicating that the CGG repeat length is a powerful predictor of neurological involvement and mortality. Intranuclear inclusions can be formed in both primary neural progenitor cells and established neural cell lines with premutation CGG repeat. A model of FXTAS using *Drosophila* has been described and it was demonstrated that premutation-length riboCGG (rCGG) repeats are both toxic and sufficient to cause neurodegeneration. These observations led to the proposal that transcription of the $CGG_{90}$ repeats leads to an RNA-mediated neurodegenerative disease and that rCGG repeat-binding proteins (RBPs) become functionally limited by their sequestration to lengthy rCGG repeats, mechanistically similar to the pathophysiology of DM1.

*Drosophila* has emerged as a premiere model system for the study of human neurodegenerative diseases within the last decade due to the realization that flies and humans share many structurally and functionally related gene families. It has been shown that genes associated with neurodegeneration could be expressed in flies, causing phenotypes remarkably similar to those of the counterpart human diseases, including polyglutamine disorders, Parkinson's disease and Alzheimer's disease. These results indicate that the molecular mechanisms of neuronal toxicity and loss are conserved between human and flies. Development of such disease models in the fly allows genetic approaches to be applied to address specific hypotheses concerning disease progression and to test candidate modifier genes or therapeutic drug compounds.

Given the high prevalence of fragile X premutation carriers among the general population (~1 in every 800 males and 250 females) and the high risk of developing FXTAS among the male carriers, it is important to develop new therapeutic interventions for FXTAS.

SUMMARY

It has been found that phospholipase A2 (PLA2) inhibitors effectively reduce the neurodegeneration associated with CGG repeats. Compounds, compositions and methods of use are thus provided that reduce PLA2 activity or expression for treatment, prophylaxis or reduction in symptoms or delay in progression of certain fragile X-associated disorders, in particular fragile X-associated tremor/ataxia syndrome (FXTAS).

In some embodiments, methods of treatment or prophylaxis of a fragile X-associated disorders, in particular a disorder associated with permutation CGG alleles such as FXTAS, are provided including administering an effective amount of an inhibitor of PLA2 to a host in need thereof.

In certain embodiments, the host has at least 55 CGG repeats in its genome. In certain other embodiments, the host has at least 100 CGG repeats in its genome. In certain embodiments, the host is suffering from a fragile X-associated tremor/ataxia syndrome. In certain embodiments, the host has been identified in radiological findings to have increased signal intensities of the middle cerebellar peduncle (MCP) and adjacent cerebellar white matter not seen in controls.

In certain embodiments, pharmaceutical compositions are provided including a PLA2 inhibitor in combination with a pharmaceutically acceptable carrier. In certain embodiments, the PLA2 inhibitor is present in a dosage level effective to treat a disorder, wherein the disorder is Fragile X-associated tremor/ataxia syndrome.

In certain embodiments, the inhibitor has an IC50 in an in vitro assay of PLA2 inhibition below 50 uM. In certain assays, the compound has an IC50 of less than 40 uM, less than 30 uM, less than 20 uM, less than 10 uM, 1 uM, 500 nM, 100 nM, 50 nM, 10 nM or less in an in vitro assay of PLA2 activity. The PLA2 inhibitor can be selected from: inhibitors of secretary phospholipase A2, cytosolic phospholipase A2, plasmalogen-selective phospholipase A2, and calcium-independent phospholipase A2. In certain embodiments the active composition includes a compound selected from: Fluocilone acetonide, Xylaxine, Dexamethasone, 4'-methoxy chalcone, citicoline, quinacrine, and combinations thereof.

Embodiments of the present disclosure also include a method of screening compounds as effective in treatment or prophylaxis of a fragile-X associated disorder that includes: 1) providing a library of compounds; 2) administering each of the compounds to a plurality of fly embryos, wherein each fly embryo includes a $CGG_{90}$ mutation linked with a hs-hid transgene, wherein upon heat shock, the expression of hs-hid will be activated; 3) exposing the fly embryos to a heat shock; 4) measuring pupae formation and adult flies in each container, wherein pupae formation and adult flies occur in containers including a compound that rescues the fly embryos of the $CGG_{90}$ mutation; and 5) selecting compounds that allowed pupae or adult fly formation.

Embodiments of the present disclosure include a kit to screen a library of compounds that includes: a plurality of fly embryos, wherein each fly embryo includes a $CGG_{90}$ mutation kinked to a hs-hid transgene that is lethal upon heat shock to fly embryos carrying the $CGG_{90}$ mutation; and a set of directions for use to screen the library of compounds.

In certain embodiments, the disclosure relates to a method of treatment a fragile X-associated disorders comprising administering an effective amount of a compound that suppresses the toxicity caused by fragile X premutation rCGG repeats to a subject in need thereof. In certain embodiments, the subject is diagnosed with a permutation CGG allele. In certain embodiments, the subject is diagnosed with FXTAS.

In certain embodiments, the compound is selected from inhibitors of phospholipase A2, secretary phospholipase A2, cytosolic phospholipase A2, plasmalogen-selective phospholipase A2, and calcium-independent phospholipase A2. In certain embodiments, the compound is selected from: fluocilone acetonide, xylaxine, dexamethasone, 4'-methoxy chalcone, citicoline, quinacrine, or salts, esters, or prodrugs thereof. In certain embodiments, the compound is selected from acetylcarnitine, 5-fluoroindole-2-carboxylic acid, propachlor, furegrelate sodium, asarylaldehyde, chromocarb, xylanzine, acetyltryptophanamide, or salts, esters, or prodrugs thereof. In certain embodiments, the compound is arachidonyl trifluoromethylketone. In certain embodiments, the compound is any provided herein substituted with one or more substituents.

In certain embodiments, the disclosure relates to a genetically engineered fly with increased expression of CG1583.

Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

DETAILED DESCRIPTION

Figure 1A:
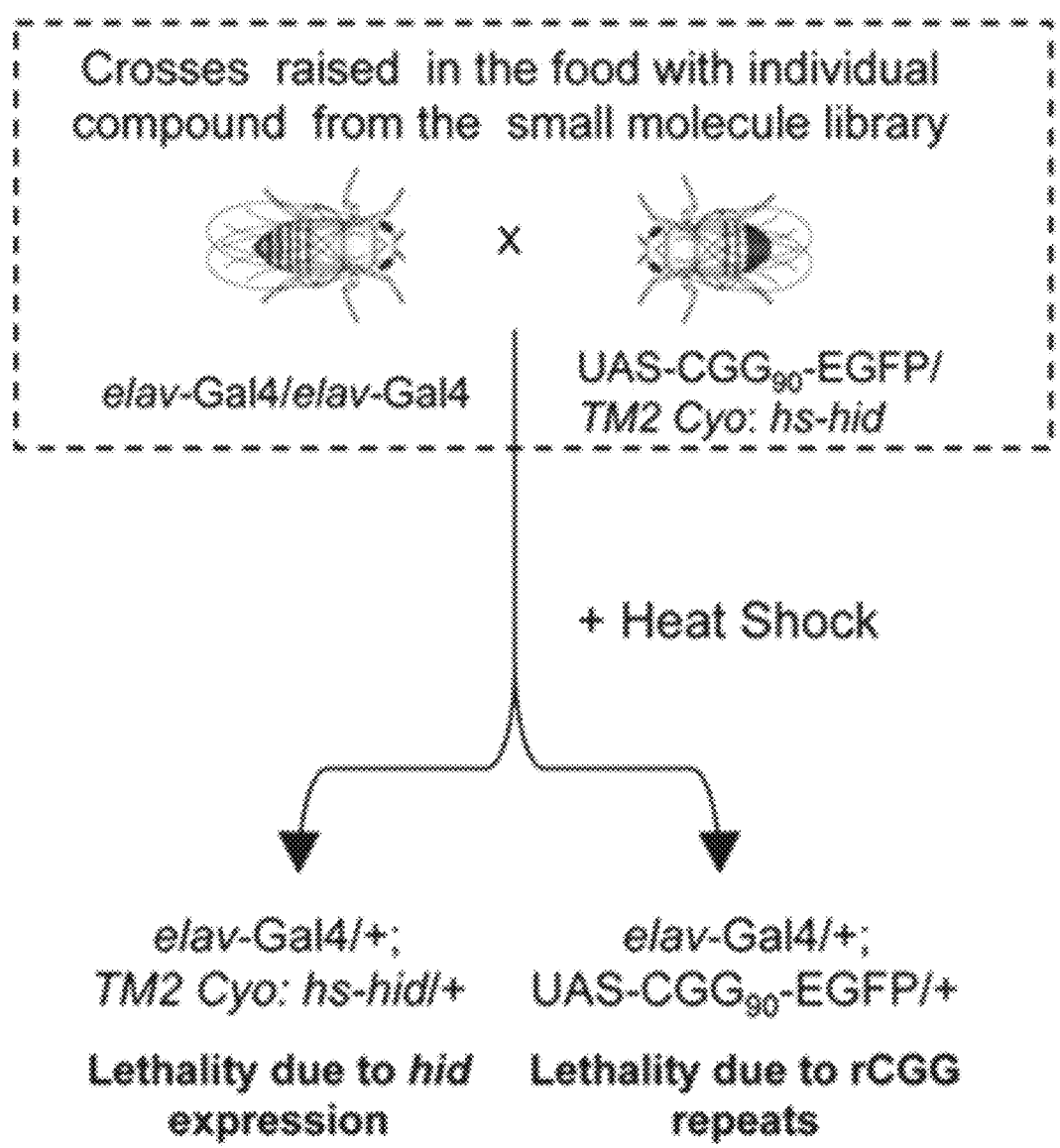
FIG. 1A schematically shows the identification of small molecules suppressing the toxicity caused by fragile X premutation rCGG repeats through a chemical screen that can suppress fragile X premutation rCGG repeat-mediated lethality. Elav-Gal4 driver and UAS-CGG90-EGFP/Cyo:hs-hid were crossed to produce progeny embryos on food supplemented with or without individual unique compounds from a library of 2000 small molecules. The progeny embryos continued to develop on food supplemented with individual drug until progeny eclosed. Relative viability was obtained by comparing numbers of adult progeny or pupae based on their genotype after heat shock was administered.

The present disclosure may be understood more readily by reference to the following detailed description and the Examples included therein. Before the present compounds, compositions and methods are disclosed and described, it is to be understood that this disclosure is not limited to specific pharmaceutical carriers, or to particular pharmaceutical formulations or administration regimens, as such may, of course, vary. It is also to be understood that the terminology used herein is for the purpose of describing particular embodiments only and is not intended to be limiting.

Definitions

As used herein, the term "subject" includes both humans, mammals (e.g., cats, dogs, horses, etc.), and other living species that are in need of treatment. A living organism can be a human or mammal. Subjects that are "predisposed" to neuronal disorders and related conditions can be defined as subjects that do not exhibit overt symptoms of one or more of these conditions but that are genetically, physiologically, or otherwise at risk of developing one or more of these conditions. Thus, compositions and agents of the present disclosure can be used prophylactically for these conditions. Further, a "composition" or "agent" can include one or more chemical compounds and/or agents, as described below. An "active composition" can include one or more "active compounds".

The term "screening" refers to the identification of one or more compounds from a library of compounds that satisfy criteria such as, but not limited to, rescuing specifically designed flies from lethal dosages of glutamate. The screening methods of the present disclosure are used to identify compounds (e.g., drug candidates to be used in an active composition) for the treatment of disorders related to the rCGG repeat mediated neurodegeneration and other diseases and disorders as described herein.

The term "derivative" means a modification to the disclosed compounds including but not limited to hydrolysis, reduction, or oxidation products of the disclosed compounds. In particular, the term encompasses opening of a nitrogen containing ring structure, including but not limited to, an imidazole of the disclosed compounds. Hydrolysis, reduction, and oxidation reactions are known in the art.

The term "therapeutically effective amount" as used herein refers to that amount of the compound being administered that will relieve to some extent one or more of the symptoms of the disorder being treated, and/or that amount that will prevent, to some extent, one or more of the symptoms of a disorder that the subject being treated is at risk of developing.

"Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990)

Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

As used herein, the term "topically active agents" refers to compositions of the present disclosure that elicit pharmacological responses at the site of application (contact in a topical application) to a host.

As used herein, the term "topically" refers to application of the compositions of the present disclosure to the surface of the skin and mucosal cells and tissues.

Throughout the specification, groups and substituents thereof may be chosen to provide stable moieties and compounds.

The disclosed compounds form salts that are also within the scope of this invention. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when an active compound of formula I contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an active compound may be formed, for example, by reacting an active compound with an amount of acid or base, such as an equivalent amount, in a medium such as one in which the salt precipitates or in an aqueous medium followed by lyophilization.

The disclosed compounds that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The disclosed compounds that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

Solvates of the compounds of the disclosure are also contemplated herein. Solvates of the compounds are preferably hydrates.

To the extent that the disclosed active compounds, and salts thereof, may exist in their tautomeric form, all such tautomeric forms are contemplated herein as part of the present disclosure.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The chiral centers of the compounds of the present disclosure can have the S or R configuration as defined by the IUPAC 1974 Recommendations.

The terms "including", "such as", "for example" and the like are intended to refer to exemplary embodiments and not to limit the scope of the present disclosure.

Discussions

Embodiments of the present disclosure include screening methods, kits for screening a library of compounds, active compositions including one or more active compounds, pharmaceutical compositions including one or more active compounds, methods of treating and/or preventing Fragile X-associated tremor/ataxia syndrome or other neurodegenerative disorders, kits for treating and/or preventing the fragile X-associated tremor/ataxia syndrome or other neurodegenerative disorders, and the like.

In general, embodiments of the present disclosure include high throughput methods of screening compounds (e.g., drug candidates) that may be used for the treatment of the fragile X-associated tremor/ataxia syndrome or other neurodegenerative disorders. The screen is a fly-based (e.g., *drosophila* (fruit fly)) compound screen, where the efficacy of the compounds is determined by scoring the number of pupae formation or the emergence of adult flies under certain incubation conditions. Compounds that satisfy the screening process may be selected as active compounds that can be used in compositions and pharmaceutical compositions to treat hosts in need of such treatment with an effective amount of the active composition.

Embodiments of the screening method are advantageous because they provide the only known approach for screening for compounds that may reverse the clinical consequence of FMR1 rCGG repeat-mediated toxicity. Moreover, using *Drosophila* provides a screen of a complex organism that is much more likely to provide a useful compound than more simple screens, such as cell based screens. Moreover, the human FMR1 gene and the *Drosophila* dFMR1 gene are highly conserved, and *Drosophila* mutants, lacking FMRP, display learning abnormalities consistent with the human phenotype. The *Drosophila* model of FXTAS has been previously established, which expresses an expanded repeat upstream of a reporter gene, EGFP, and demonstrates a direct involvement of fragile X premutation rCGG repeats in the pathogenesis of human FXTAS. In this model, the GAL4-UAS system was used to drive expression of the transgene in different tissues, including the eye of the fly. Flies showed neurodegeneration of the eye and inclusion formation in the nucleus and cytoplasm that mimic the human phenotypes.

In general, embodiments of the present disclosure provide an active composition including one or more active compounds that can be used to treat and/or prevent the fragile X-associated tremor/ataxia syndrome or other neurodegenerative disorders caused by the rCGG repeat-mediated toxicity. For example, the active composition can be used to treat and/or prevent FXTAS. In addition, the active composition can be used to treat and/or prevent anxiety disorders and disorders of memory, including but not limited to, Alzheimer's disease. Further, the active composition can be used to treat and/or prevent glutamate excitotoxity disorders and diseases such as, but not limited to, Huntington's disease, Parkinson's disease and the consequence of a stroke.

Screening

Embodiments of the present disclosure include high throughput methods of screening compounds (e.g., drug candidates) that may be used for the treatment of the fragile X-associated tremor/ataxia syndrome. In addition, embodiments of the present disclosure include high throughput methods of screening compounds (e.g., drug candidates) that may be used for the treatment of related anxiety disorders and disorders of memory.

In particular, embodiments of the present disclosure include methods of screening compounds using a *drosophila* (fruit fly) based compound screen to identify drug candidates for the treatment of the fragile X-associated tremor/ataxia syndrome or other neurodegenerative disorders. The fly carrying the $CGG_{90}$ dFmr1 premutation exhibits neuronal and behavioral defects similar to those reported in FXTAS mouse models and in human patients. It was found that expression of dFmr1 premutation rCGG repeats in the central nervous system leads to lethality in early embryonic development. A fly line of UAS-CGG90-EGFP transgene balanced with Cyo balancer carrying hs-hid transgene was generated. Upon heat shock, the expression of hid was activated, which led to cell death and lethality in the $CGG_{90}$ dFmr1 premutation fly embryos. As exhibited in FIG. 1, upon heat shock during early embryonic development, no viable flies or pupae was produced.

The mutant embryos were placed into an appropriate container (e.g., a 96-well container) containing a food with or without a compound from a library of drugs candidates. 5 µM and 40 µM of individual compounds from a library of 2,000 FDA approved drugs and natural products (The Spectrum Collection™) were screened. Vials were then kept at 25° C. for 10 to 15 days to score for viability. The efficacy of the drug candidate was determined by scoring the number of pupae formation or the emergence of adult flies after a certain time frame. Embodiments of the present disclosure provide a screen for compounds that directly and indirectly regulate dFmr1 rCGG repeat mediated toxicity and rescue mutant flies from heat shock induced lethality. Additional details regarding the active compositions and disorders are described in the Examples below.

Compositions of Matter

In general, the active compositions including one or more active compounds can be used to treat and/or prevent fragile X-associated tremor/ataxia syndrome or other neurodegenerative disorders such as, but not limited to, the FXTAS, anxiety-related disorders, memory-related disorders, and the like.

In certain embodiments, the compounds are inhibitors of PLA2 activity. In certain embodiments, the inhibitor has an IC50 in an in vitro assay of PLA2 inhibition below 50 uM. In certain assays, the compound has an IC50 of less than 40 uM, less than 30 uM, less than 20 uM, less than 10 uM, 1 uM, 500 nM, 100 nM, 50 nM, 10 nM or less in an in vitro assay of PLA2 activity. Assays of PLA2 activity are commercially available and include the EnzChekR Phospholipase A2 Assay Kit (Invitrogen) which provides a simple fluorometric method designed for continuous monitoring of phospholipase A2 (PLA2), PLA2 test systems that are based on the use of radioactive phospholipids [Lucas and Dennis, Distinguishing phospholipase A2 types in biological samples by employing group-specific assays in the presence of inhibitors, Prostaglandins Other Lipid Mediators 77 (2005), pp. 235-248] or the chromatographic separation of substrate and product by HPLC [Schmitt and Lehr, HPLC assay with UV spectrometric detection for the evaluation of inhibitors of cytosolic phospholipase A2, J. Pharm. Biomed. Anal. 35 (2004), pp. 135-142] or a pyrene-modified phospholipid as substrate [Leslie and Gelb, Assaying phospholipase A2 activity, Methods Mol. Biol. 284 (2004), pp. 229-242; Boehl, et al. (2006) Phospholipase A2 inhibition at different substrate concentrations Analytical Biochem. 359:280-82].

The PLA2 inhibitor can be selected from inhibitors of secretary phospholipase A2, cytosolic phospholipase A2, plasmalogen-selective phospholipase A2, and calcium-independent phospholipase A2. Many PLA2 inhibitors are known to exert their neuroprotective effects by suppressing or lowering transcription of genes for PLA2 isozymes. Known Phospholipase A2 inhibitors including, but not limited to, quinacrine, chloroquine, arachidonyl trifluoromethyl ketone (ATK), methyl arachidonyl fluorophosphonate, benzenesulfonamides, alkoxybenzamidines, 3-(Pyrrol)-2-propionic acid, 2-Oxoamide, 1,3-disubstituted propan-2-ones, 2-(2-benzyl-4-chlorophenoxy)ethyldimethyl-n-oc-tadecyl-ammonium chloride, 2-(2-benzyl-4-chloro-phenoxy)ethyldimethyl-n-octyl-ammonium bromide, citicoline, bromoenol lactone, cytidine 5-diphosphoamines, pyrrophenone, pyrrolidine dithiocarbamate, and vitamin E, not only inhibit phospholipase A2 activity and immunoreactivity but also prevent neurodegeneration. In certain embodiments the active composition includes a compound selected from: Fluocilone acetonide, Xylaxine, Dexamethasone, 4'-methoxy chalcone, citicoline, quinacrine, and combinations thereof. The active composition can include one or more active compounds such as, but not limited to, Acetyl carnitine, Acetyltryptophanamide, 5'-fluoroindole-2 careboxylic acid, Chromocarb, Asarylaldehyde, Furegrelate sodium, Propachlor, Fluocilone acetonide, Xylaxine, Dexamethasone, 4'-methoxy chalcone, phospholipase A2 (PLA2) inhibitors, and combinations thereof.

In particular, the phospholipase A2 (PLA2) inhibitors can include, but is not limited to, fluocilone acetonide, arachidonic acid and eicosanoids, derivatives of each, precursors thereof, and the like. In an embodiment, the active composition includes fluocilone acetonide.

Where such forms exist, the active compounds of the active composition (e.g., members of acetyl carnitine, acetyltryptophanamide, 5'-fluoroindole-2 careboxylic acid, chromocarb, asarylaldehyde, furegrelate sodium, propachlor, fluocilone acetonide, xylaxine, dexamethasone, 4'-methoxy chalcone, phospholipase A2 (PLA2) inhibitors, and combinations thereof) can include analogues, compound homologues, compound isomers, or derivatives thereof, that can function in a similar biological manner as the active compounds of the active composition to treat and/or prevent the fragile x associated tremor/ataxia syndrome and other neurodegenerative disorders described herein including anxiety disorders and memory disorders and related conditions in a host. In addition, where such forms exist, the active compounds of the active composition can include pharmaceutically acceptable salts, esters, and prodrugs of the active compounds of the active composition described or referred to herein.

Based on embodiments of the present disclosure and the discussion in the Examples, a dosage regime for the active composition can be developed. In general, the starting dose of most Phase I clinical trials is based on preclinical testing, and is usually quite conservative. A standard measure of toxicity of a drug in preclinical testing is the percentage of animals (rodents) that die because of treatment. The dose at which 10% of the animals die is known as the LD10, which has in the past often correlated with the maximal-tolerated dose (MTD) in humans, adjusted for body surface area. The adjustment for body surface area includes host factors such as, for example, surface area, weight, metabolism, tissue distribution, absorption rate, and excretion rate. Thus, the standard conservative starting dose is one tenth the murine LD10, although it may be even lower if other species (i.e., dogs) were more sensitive to the drug. It is anticipated that a starting dose for the active composition in Phase I clinical trials in humans will be determined in this manner. This dosing regimen is discussed in more detail in Freireich E J, et al., Cancer Chemother Rep 50:219-244, 1966, which is incorporated herein by reference.

As stated above, a therapeutically effective dose level will depend on many factors. In addition, it is well within the skill of the art to start doses of the active composition at relatively low levels, and increase the dosage until the desired effect is achieved.

Pharmaceutical Compositions

Embodiments of the present disclosure provide compositions and pharmaceutical compositions including the active composition (e.g., one or more active compounds) in an effective amount to treat and/or prevent a disorder such as those described herein.

Pharmaceutically active compositions and dosage forms of the disclosure include a pharmaceutically acceptable salt of disclosed or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof.

Pharmaceutical compositions and unit dosage forms of the disclosure typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art.

Pharmaceutical unit dosage forms of the compounds of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure will typically vary depending on their use. For example, a dosage form used in the acute treatment of a disease or disorder may contain larger amounts of the active ingredient, for example the disclosed compounds or combinations thereof, than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Typical pharmaceutical compositions and dosage forms comprise one or more excipients. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition.

The disclosure further encompasses pharmaceutical compositions and dosage forms that include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the compounds of the disclosure comprise a pharmaceutically acceptable salt, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, and more preferably in an amount of from 50 mg to 500 mg.

Additionally, the compounds and/or compositions can be delivered using lipid- or polymer-based nanoparticles. For example, the nanoparticles can be designed to improve the pharmacological and therapeutic properties of drugs administered parenterally (Allen, T. M., Cullis, P. R. Drug delivery systems: entering the mainstream. Science. 303(5665): 1818-22 (2004)).

Oral Dosage Forms

Pharmaceutical active compositions of the disclosure that are suitable for oral administration can be presented as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Typical oral dosage forms of the compositions of the disclosure are prepared by combining the pharmaceutically acceptable salt of disclosed compounds in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Due to their ease of administration, tablets and capsules represent the most advantageous solid oral dosage unit forms, in which case solid pharmaceutical excipients are used. If desired, tablets can be coated by standard aqueous or non-aqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103® and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the disclosure. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used to form pharmaceutical compositions and dosage forms of the disclosure include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Plano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

This disclosure further encompasses lactose-free pharmaceutical compositions and dosage forms, wherein such compositions preferably contain little, if any, lactose or other mono- or di-saccharides. As used herein, the term "lactose-free" means that the amount of lactose present, if any, is insufficient to substantially increase the degradation rate of an active ingredient.

Lactose-free compositions of the disclosure can comprise excipients which are well known in the art and are listed in the USP (XXI)/NF (XVI), which is incorporated herein by reference. In general, lactose-free compositions comprise a pharmaceutically acceptable salt of a compound in the active composition, a binder/filler, and a lubricant in pharmaceutically compatible and pharmaceutically acceptable amounts. Preferred lactose-free dosage forms comprise a pharmaceutically acceptable salt of the disclosed compounds, microcrystalline cellulose, pre-gelatinized starch, and magnesium stearate.

This disclosure further encompasses anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms

Pharmaceutically acceptable salts of the disclosed active compounds can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

One embodiment of the disclosure encompasses a unit dosage form that includes a pharmaceutically acceptable salt of the disclosed compounds (e.g., a sodium, potassium, or lithium salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the disclosure. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the disclosure include, but are not limited to, the OROS® Push-Pull®, Delayed Push-Pull®, Multi-Layer Push-Pull®, and Push-Stick® Systems, all of which are well known. See, e.g., worldwide website alza.com. Additional OROS® systems that can be used for the controlled oral delivery of compounds and compositions of the disclosure include OROS®-CT and L-OROS®; see, Delivery Times, vol. 11, issue II (Alza Corporation).

Conventional OROS® oral dosage forms are made by compressing a drug powder (e.g., a salt of a compound of the active composition) into a hard tablet, coating the tablet with cellulose derivatives to form a semi-permeable membrane, and then drilling an orifice in the coating (e.g., with a laser). Kim, Chemg-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively delivery drugs with low water solubility. Because salts of compound of the active composition and complexes of this disclosure (e.g., an compound sodium salt of the active composition) may be far more soluble in water than an active compound itself, they may be well suited for osmotic-based delivery to patients. This disclosure does, however, encompass the incorporation of an active compound, and non-salt isomers and isomeric mixtures thereof, into OROS® dosage forms.

A specific dosage form of the active compositions of the disclosure includes: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent the exit orifice and in direct or indirect contacting relationship with the expandable layer; and a flow-promoting layer interposed between the inner surface of the wall and at least the external surface of the drug layer located within the cavity, wherein the drug layer includes a salt of a compound of the active composition, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the disclosure includes: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of a compound of the active compound, or a polymorph, solvate, hydrate, dehydrate, co-crystal, anhydrous, or amorphous form thereof. See U.S. Pat. No. 6,342,249, the entirety of which is incorporated herein by reference.

Parenteral Dosage Forms

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Compounds that alter or modify the solubility of a pharmaceutically acceptable salt of an active composition disclosed herein can also be incorporated into the parenteral dosage forms of the disclosure, including conventional and controlled-release parenteral dosage forms.

Topical, Transdermal and Mucosal Dosage Forms

Topical dosage forms of the disclosure include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

Transdermal and mucosal dosage forms of the active compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466; 465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of a compound of the active compositions of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of a compound of the active composition can be used to further adjust the properties of the resulting composition.

Kits

In some embodiments, active ingredients of the pharmaceutical compositions of the disclosure may not be administered to a patient at the same time or by the same route of administration. This disclosure therefore encompasses kits which, when used by the medical practitioner, can simplify the administration of appropriate amounts of active ingredients to a patient.

A typical kit includes a unit dosage form of a pharmaceutically acceptable salt of an active compound of the active composition. In particular, the pharmaceutically acceptable salt of an active compound of an active composition is the sodium, lithium, or potassium salt, or a polymorph, solvate, hydrate, dehydrate, co-crystal, anhydrous, or amorphous form thereof. A kit may further include a device that can be used to administer the active ingredient. Examples of such devices include, but are not limited to, syringes, drip bags, patches, and inhalers. The kit may include directions for use of the kit.

Kits of the disclosure can further include pharmaceutically acceptable vehicles that can be used to administer one or more active ingredients (e.g., an active compound). For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration.

Examples of pharmaceutically acceptable vehicles include, but are not limited to: water for injection USP; aqueous vehicles such as, but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In another embodiment, a kit for screening compounds for drug candidates includes a plurality of fly embryos. Each fly embryo includes a dFmr1 $CGG_{90}$ mutation linked to a hs-hid transgene (where heat shock is lethal to fly embryos of the dFmr1 $CGG_{90}$ mutation) and a set of directions for use to screen a library of compounds.

EXAMPLES

Identification of Compounds that Suppress the Toxicity Caused by Fragile X Premutation rCGG Repeats through a Chemical Screen A *Drosophila* disease model of FXTAS and provided experimental evidence that fragile X premutation rCGG repeats alone are sufficient to cause neurodegeneration in a repeat-dosage manner. See Jin et al., Neuron, 2003, 39:739-747. Flies with modest expression of fragile X premutation rCGG90 repeats exclusively in the neurons do not reach adulthood. Lethality occurs primarily during embryonic development before larval formation. Taking advantage of this lethality, a high-throughput strategy was designed to screen chemical libraries for small molecules relevant to FXTAS. the UAS-CGG90-EGFP transgene was balanced with a chromosome carrying a curly wing (Cyo) marker recombined with a heat shock-inducible apoptotic hid (hs-hid) transgene (w1118, UAS-CGG90-EGFP/TM2 Cyo:hs-hid). Next, the viability of adult progeny was tested using the Drosophila GAL4/UAS system. crosses of UAS-CGG90-EGFP/TM2 Cyo:hs-hid were performed with homozygous pan-neuronal elav-Gal4 driver. There was an absence of heterozygous non-Cyo adult progeny (elav-GAL4/+; UAS-CGG90-EGFP/+), which confirmed that rCGG90 repeat expression in neurons leads to lethality. The only living progenies would carry elav-GAL4/+; +/TM2 Cyo:hs-hid. Furthermore, upon heat shock, the progenies carrying elav-GAL4/+; +/TM2 Cyo:hs-hid also died, because the expression of hid leads to cell death and lethality at embryonic stages that are otherwise viable.

Since the rescue of the lethality was an easily scored phenotype, one is able to use this assay to conduct a chemical screen to identify the small molecules that can improve/restore the viability of the flies expressing fragile X premutation rCGG repeats. As depicted in schematic representation (FIG. 1A), crosses between elav-GAL4 and UAS-CGG90-EGFP/TM2 Cyo:hs-hid were raised as well as control flies into food supplemented with 40 μm of individual unique compounds from a library of 2000 US Food and Drug Administration (FDA)-approved drugs and natural products (The Spectrum Collection, MicroSource Discovery Systems, Inc.). At day 2, crosses were subsequently heat shocked to eliminate (elav-GAL4/+; +/TM2 Cyo:hs-hid) progenies, and the vials were then kept at 25° C. for 10-15 days to score for any of the viable (elav-GAL4/+; UAS-CGG90-EGFP/+) flies that are otherwise lethal.

Figure 1B:
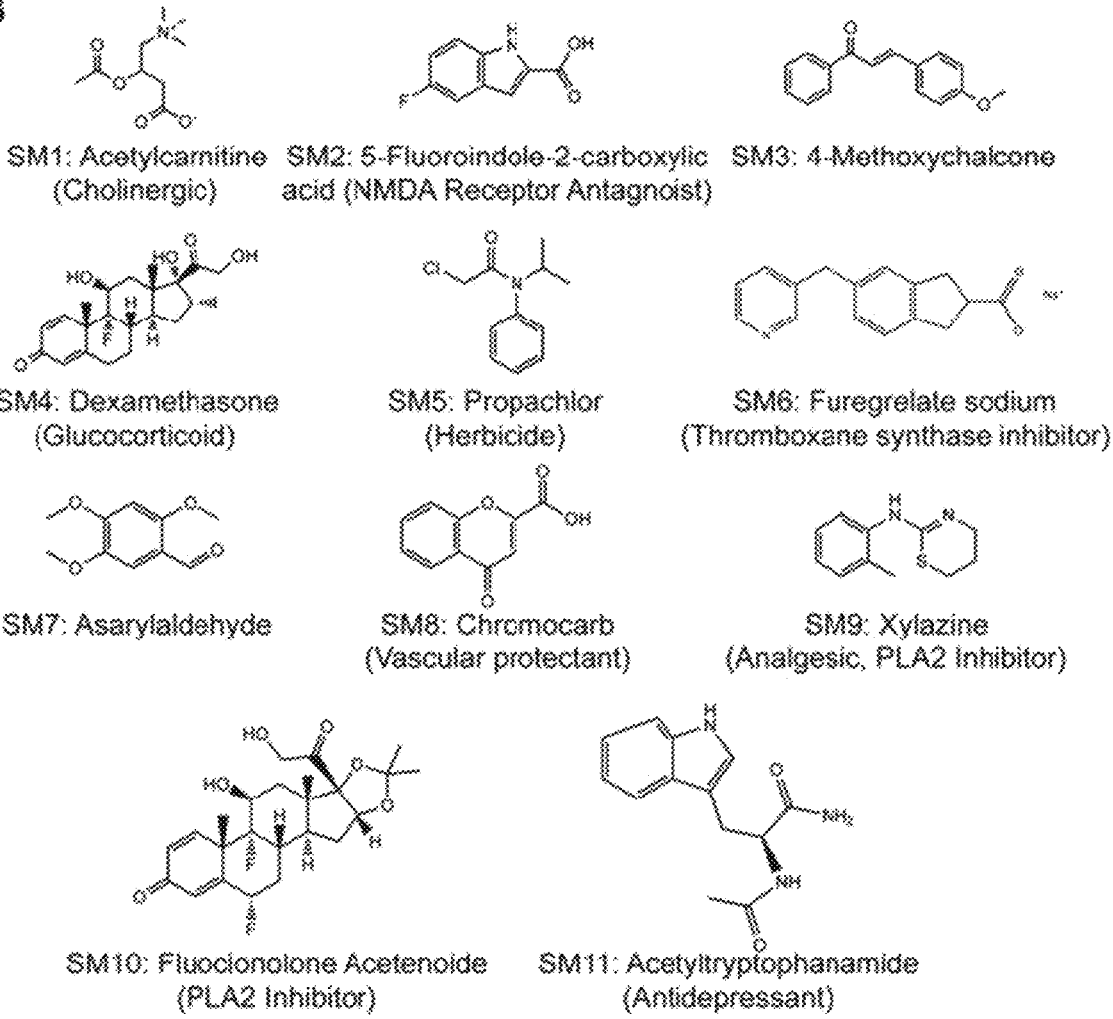
FIG. 1B shows the chemical structures of 11 small molecules that could suppress the toxicity caused by fragile X premutation rCGG repeats.

Among the 2000 compounds initially screened, 58 were found to result in either puparium formation or the emergence of adult non-Cyo progeny (elav-GAL4/+; UAS-CGG90-EGFP/+). Since the puparium formation could also represent dead (elav-GAL4/+; +/TM2 Cyo:hs-hid) progeny simply due to heat shock, the top 35% (20 of 58 compounds) were selected based on the percentage of recovered flies or pupae from the crosses for further validation. Among these 20 compounds, 11 were validated using large-scale viability assays (FIG. 1B). The confirmed compounds belong to several biochemically distinct pathways, with several of them having the potential to target inflammatory pathways (FIG. 1B).

Figure 2A:
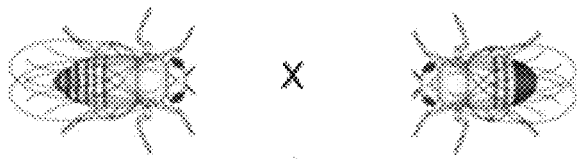
FIG. 2A illustrates the identification of small molecules that can ameliorate the locomotion deficits caused by fragile X premutation rCGG repeats. Nervana-GAL4 driver and UAS-CGG90-EGFP/Cyo were crossed to produce progeny embryos on food supplemented with or without selected compounds as indicated. Adult progeny of genotype UAS-CGG90-EGFP/nervana were selected and 32 female virgins 48 h old were subsequently monitored for locomotor activity continuously for several weeks. The locomotion of 32 flies that were fed with fly food containing the compound each time were simultaneously monitored.

Identification of Compounds that can Ameliorate the Locomotion Deficits Caused by Fragile X Premutation rCGG Repeats To further validate these compounds, a secondary behavioral assay was developed. In this assay, UAS-CGG90-EGFP transgenic flies were crossed with nervana-GAL4, which could drive the expression of fragile X rCGG repeats in CNS, albeit weakly, allowing us to analyze adult flies for locomotion deficits. The expression of rCGG repeats leads to locomotion defects (FIG. 2A). As shown in FIG. 2A, the cross between UAS-CGG90-EGFP/TM2 Cyo and nervana-GAL4 was set up in food that was supplemented with each compound. The progeny flies (UAS-CGG90-EGFP/nervana-GAL4) were collected to monitor locomotion. To continuously monitor the locomotion for a given fly, a Drosophila Activity Monitor (DAM) system was established for this purpose. See Pfeiffenberger et al., Locomotor activity level monitoring using the Drosophila Activity Monitoring (DAM) System. Cold Spring Harb. Protoc. 2010.

Figure 2B:
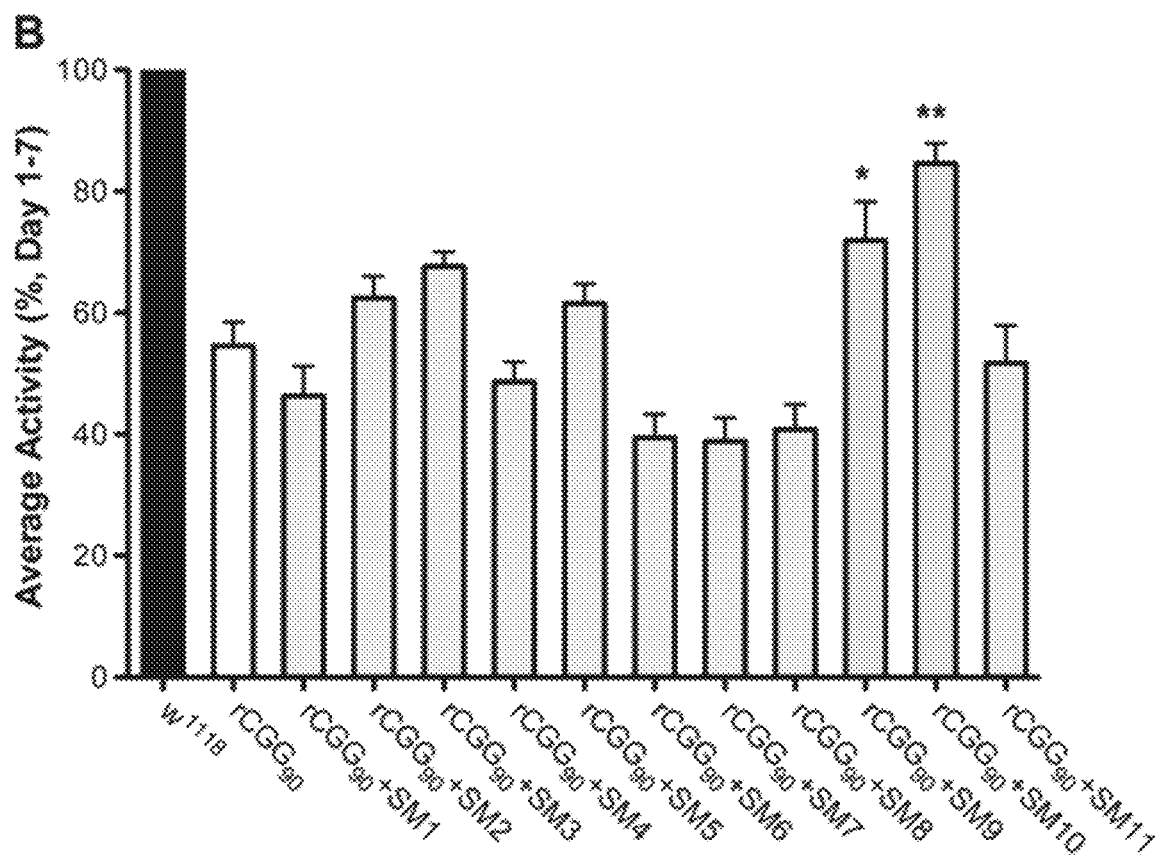
FIG. 2B shows data on the percentage of mean locomotor activity over a period of 7 days was plotted for selected drugs. Error bars indicate SEM. **$P<0.001$, *$P<0.01$.

For each individual compound, the locomotion of 32 flies were simultaneously monitored that were fed with fly food containing the compound each time. The data were collected and analyzed for locomotor activity (FIG. 2B). Each drug treatment was repeated at least three times. Fluocinolone acetonide and xylazine could significantly ameliorate the locomotion defects induced by fragile X premutation rCGG repeats (FIG. 2B).

Figure 3A:
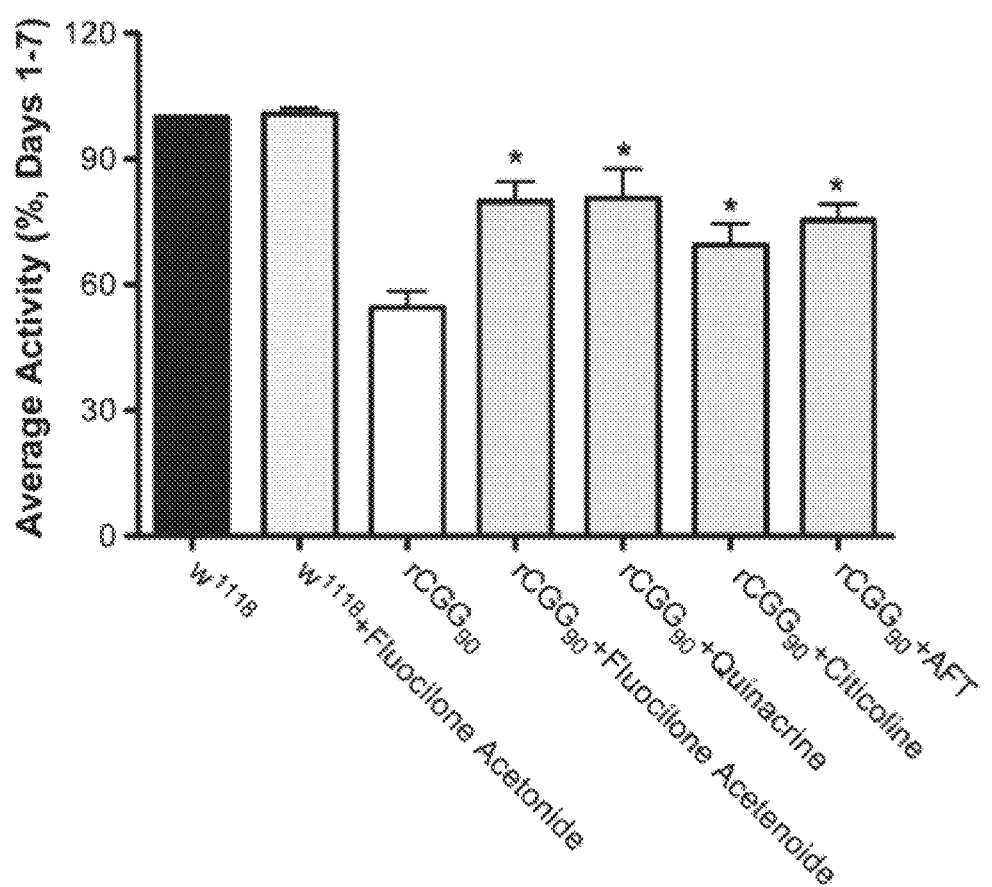
FIG. 3A shows data indicating phospholipase A2 inhibitors can specifically suppress locomotion deficits caused by fragile X premutation rCGG repeats. The percentage of mean locomotor activity over a period of 7 days was plotted for multiple PLA2 inhibitors. Error bars indicate SEM; *$P<0.001$.
Figure 3B:
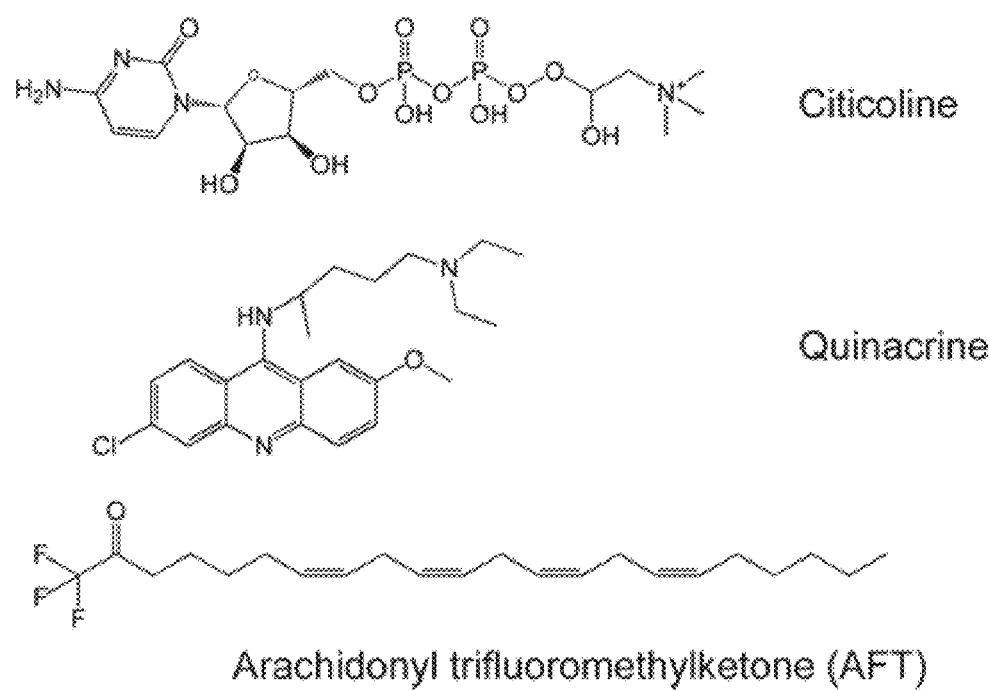
FIG. 3B illustrates the chemical structures of certain PLA2 inhibitors used for locomotion assays.

Phospholipase A2 Inhibitors can Specifically Suppress Locomotion Deficits Caused by Fragile X Premutation rCGG Repeats Fluocinolone acetonide is an inhibitor of phospholipase A2 (PLA2). The PLA2 family includes secretory phospholipase A2, cytosolic phospholipase A2, plasmalogen-selective phospholipase A2 and calcium-independent phospholipase A2. It is generally thought that the release of arachidonic acid by cytosolic PLA2 is the rate-limiting step in the generation of eicosanoids and platelet-activating factor. These lipid mediators play roles in the initiation and modulation of inflammation and oxidative stress. The regulation of PLA2 activity is important for maintaining basal levels of arachidonic acid and eicosanoids for performing normal function. Our finding that fluocinolone acetonide could suppress both lethality and locomotion deficits caused by fragile X premutation rCGG repeats raised the possibility that PLA2 inhibitors in general could suppress rCGG-mediated neurodegeneration. To test this hypothesis, other known PLA2 inhibitors were used for locomotion assays. Cytidine 5'diphospho-choline (citicoline) inhibits cPLA2 activity and lowers the concentration of free fatty acids in a dose- and time-dependent manner. Likewise, release of arachidonic acid can be blocked by quinacrine and arachidonyl trifluoromethylketone (FIG. 3A). Significant improvements were observed in locomotion in flies expressing rCGG repeats for all the PLA2 inhibitors, whereas these compounds had no significant impact on the locomotor activity of wild-type flies (FIG. 3A). These observations strongly suggest that PLA2 activity is altered by fragile X premutation rCGG repeats, and PLA2 inhibitors could suppress rCGG-mediated neurodegeneration.

Figure 4A:
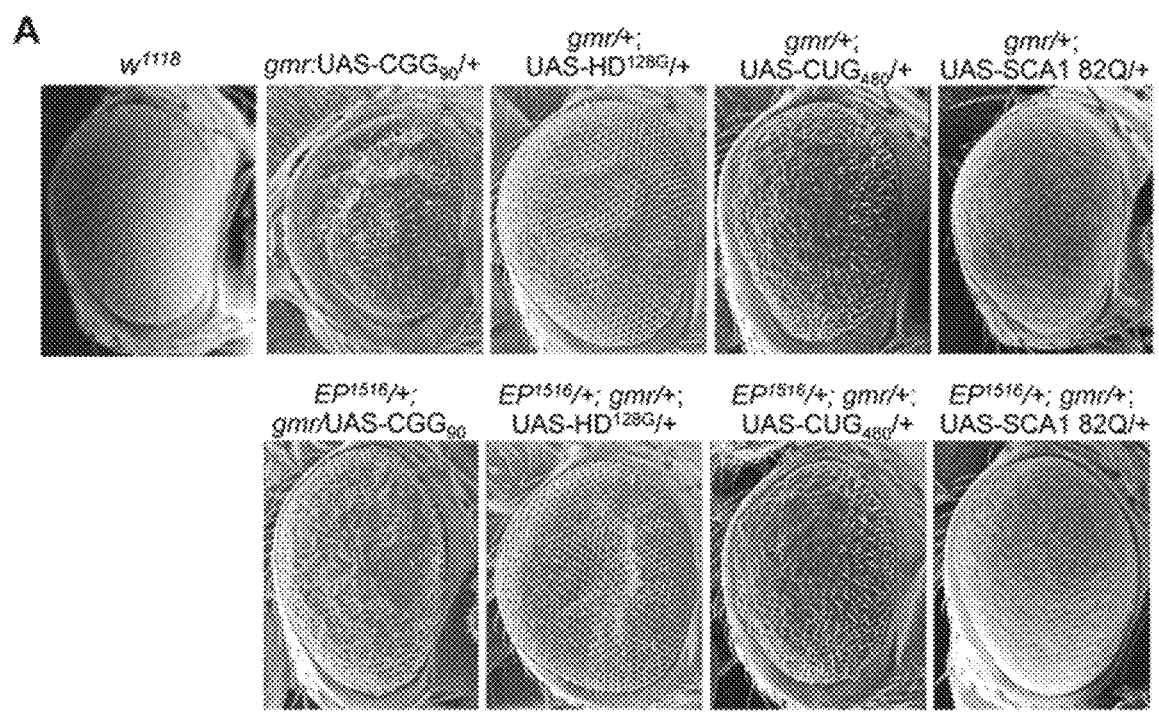
FIG. 4A shows Scanning electron microscopic eye images indicating that CG1583, a predicted *Drosophila* ortholog of PLA2, specifically modulates fragile X premutation rCGG-mediated neurodegeneration. CG1583 modulates rCGG-mediated neurodegeneration in fly. Top panel shows control (w1118) fly (column 1); and gmr-GAL4 directed expression of the following transgenes: UAS-(CGG)90-EGFP (column 2), UAS-HD128G/+ (column 3); UAS-CUG480/+ (column 4); UAS-SCA1 82Q/+ (column 5). Bottom panel shows the modulation of the eye phenotype in fly expressing CGG90-EGFP with the heterozygous background of CG1583EP1516 mutation (column 1); column 2: fly expressing UAS-HD128G/+ in the heterozygous background of CG1583EP1516 mutation (column 2); fly expressing UAS-CUG480/+ in the heterozygous background of CG1583EP1516 mutation (column 3); fly expressing UAS-SCA1 82Q/+ in the heterozygous background of CG1583EP1516 mutation (column 4). The suppression between the genotypes was scored blindly as normal, moderate or severe.
Figure 4B:
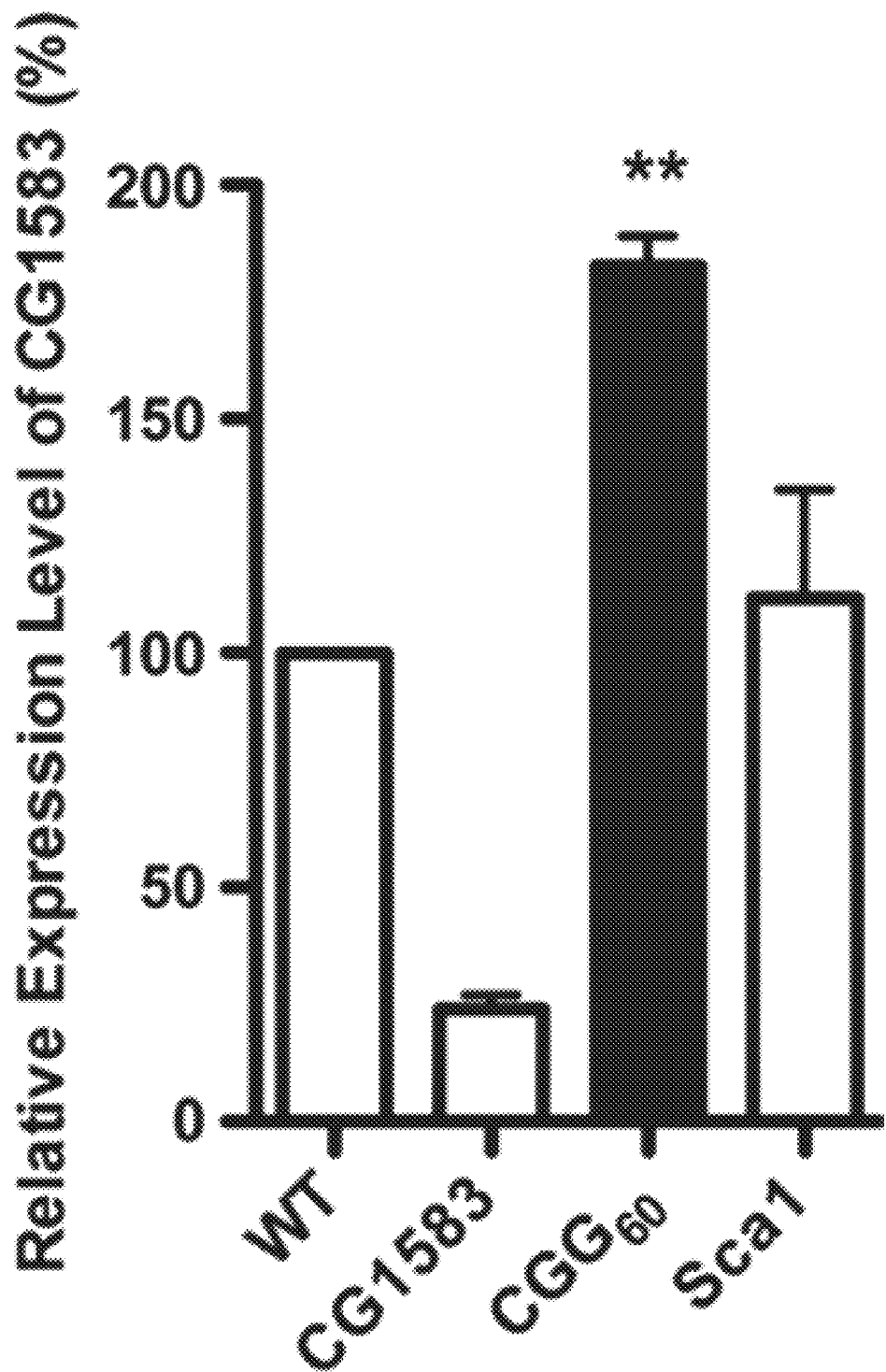
FIG. 4B shows data on quantitative analysis of the CG1583 mRNA levels by real-time PCR from the adult brains of flies with the following genotypes: wild-type (w1118); CG1583EP1516; elav; rCGG60-EGFP; and UAS-SCA1 82Q/+. Housekeeping ribosomal protein 32 (Rp132) mRNA was used as an internal control (mean±SEM; n=3).

Candidate Genetic Screen Identifies the Drosophila Ortholog of the Phospholipase A2 Gene, CG1583, as the Modulator of rCGG Repeat-mediated Neuronal Toxicity The role of PLA2 isoforms in mediating fragile X premutation rCGG repeat-mediated neuronal toxicity was explored. In Drosophila, the genes for some PLA2 isoforms have been mapped, but none has been cloned and fully characterized; therefore, to examine the role of the PLA2 pathway in FXTAS, the Kyoto encyclopedia of genes and genomes (KEGG) human database was used to identify and collect known pathways that are related to lipid metabolism and PLA2 activity. Reference maps were then created for the PLA2 pathways and looked at for the genes and pathways that are related in flies. Mutations in some of the genes of the pathway were identified and a genetic screen based on the fragile X premutation rCGG repeat-mediated neurodegenerative eye phenotype was conducted. The screen involved directing the expression of fragile X premutation-length rCGG repeats to the eye with the gmr-GAL4 driver. This was followed by crossing gmr-GAL4, UAS-(CGG)90-EGFP transgenic flies with flies mutant in genes coding for lipid metabolism and PLA2 activity identified from the reference KEGG map. The progenies were examined for potential suppression or enhancement of the disorganized eye phenotype by comparison with control rCGG flies. Through this screen, an EP line, CG1583EP1516 (a *Drosophila* homolog of PLA2 gene), was identified that could modulate the rCGG-mediated neurodegeneration (FIG. 4A). Since CG1583EP1516 is an EP insertion that is supposed to activate the transcription of the adjacent gene, quantitative reverse transcription polymerase chain reaction (RT-PCR) using the RNAs isolated from age-matched brains was performed to determine the expression of CG1583 in both CG1583EP1516 and control (w1118) flies. CG1583EP1516 specifically disrupted the CG1583 gene and led to the partial loss of gene expression (FIG. 4B). An adjacent gene, Traf 6, did not interact genetically with rCGG-mediated neurodegeneration. This modulation was further confirmed using an RNAi UAS line (GIIIs-PLA2 v50353) that could express dsRNAs against CG1583 in the presence of a GAL4 driver.

CG1583 is a Specific Modifier of rCGG-mediated Neurodegeneration

Because PLA2 is linked to several neurological disorders, whether CG1583 is a specific modifier of rCGG-mediated toxicity was determine. CG1583EP151 was crossed with fly models of other neurodegenerative disorders. Like fragile X premutation rCGG repeats, transgenic flies expressing mutant Huntington's disease (HD), cytosine uracil guanine (CUG) repeats or SCA1 show rough eye phenotype when crossed with gmr-Gal4 driver. As shown in FIG. 4A, the partial loss of CG1583 had no effect on the neuronal eye degeneration caused by mutant HD, CUG repeats or SCA1. The expression of CG1583 using RNAs isolated was determined from the age- and sex-matched brains of w1118 and flies expressing CGG60 repeats in neurons (elav/+; UAS-CGG60-EGFP). Fragile X premutation rCGG repeats, but not SCA1, could cause increased expression of CG1583 in fly brains (FIG. 4B). These results together suggest that CG1583, a *Drosophila* ortholog of PLA2, is a specific modulator of rCGG-mediated neurodegeneration.

Fluocilone Acetonide

It was found that supplementing 40 microM of fluocilone acetonide in the food yielded 7.5% recovery of dFmr1 $CGG_{90}$ mutant flies compared with 0% on food alone. In addition, fluocilone acetonide -treated dFmr1 $CGG_{90}$ mutant flies demonstrated significant suppression of the locomotion activity deficit. Locomotion activity deficit is a significant symptom in FXTAS patients, and was shown to be abnormal in FXTAS flies. The treatment of fluocilone acetonide increased the percentage of normal locomotion activity in dFmr1 $CGG_{90}$ mutant flies from 50% to 99%. Based on these novel findings, it can be concluded that fluocilone acetonide plays an important role in regulating the rCGG repeat-mediated function. This indicates that fluocilone acetonide may be used for the treatment of fragile X-associated tremor/ataxia syndrome and other neurodegenerative disorders, including anxiety disorders and memory disorders.

Dexamethasone

It was found that supplementing 40 microM of dexamethasone in the food yielded 5% recovery of dFmr1 $CGG_{90}$ mutant flies compared with 0% on food alone. In addition, dexamethasone-treated dFmr1 $CGG_{90}$ mutant flies demonstrated significant suppression of the locomotion activity deficit. Locomotion activity deficit is a significant symptom in FXTAS patients, and was shown to be abnormal in FXTAS flies. The treatment of dexamethasone increased the percentage of normal locomotion activity in dFmr1 $CGG_{90}$ mutant flies from 50% to 90%. Based on these novel findings, it can be concluded that dexamethasone plays an important role in regulating the rCGG repeat-mediated function. This indicates that dexamethasone may be used for the treatment of fragile X-associated tremor/ataxia syndrome and other neurodegenerative disorders, including anxiety disorders and memory disorders.

Xylaxine

It was found that supplementing 40 microM of xylaxine in the food yielded 5% recovery of dFmr1 CGG90 mutant flies compared with 0% on food alone. In addition, xylaxine -treated dFmr1 CGG90 mutant flies demonstrated significant suppression of the locomotion activity deficit. Locomotion activity deficit is a significant symptom in FXTAS patients, and was shown to be abnormal in FXTAS flies. The treatment of xylaxine increased the percentage of normal locomotion activity in dFmr1 CGG90 mutant flies from 50% to 80%. Based on these novel findings, it can be concluded that xylaxine plays an important role in regulating the rCGG repeat-mediated function. This indicates that xylaxine may be used for the treatment of fragile X-associated tremor/ataxia syndrome and other neurodegenerative disorders including anxiety disorders and memory disorders.

4'-Methoxychalcone

It was found that supplementing 40 microM of 4'-methoxy chalcone in the food yielded 3% recovery of dFmr1 $CGG_{90}$ mutant flies compared with 0% on food alone. In addition, 4'-methoxy chalcone-treated dFmr1 $CGG_{90}$ mutant flies demonstrated significant suppression of the locomotion activity deficit. Locomotion activity deficit is a significant symptom in FXTAS patients, and was shown to be abnormal in FXTAS flies. The treatment of 4'-methoxy chalcone increased the percentage of normal locomotion activity in dFmr1 $CGG_{90}$ mutant flies from 50% to 75%. Based on these novel findings, it can be concluded that 4'-methoxy chalcone plays an important role in regulating the rCGG repeat-mediated function. This indicates that 4'-methoxy chalcone may be used for the treatment of fragile X-associated tremor/ataxia syndrome and other neurodegenerative disorders including anxiety disorders and memory disorders.

What is claimed:

1. A method of treating a fragile X-associated disorder comprising administering an effective amount of a compound selected from xylazine, 4'-methoxychalcone, 5 fluoroindole-2-carboxylic acid, propachlor, furegrelate, asarylaldehyde, chromocarb, acetyltryptophanamide, salts, esters, and prodrugs thereof to a subject in need thereof.

2. The method of claim 1, wherein the subject is diagnosed with a permutation CGG allele.

3. The method of claim 1, wherein the subject is diagnosed with fragile X-associated tremor and ataxia syndrome.

* * * * *